United States Patent
Benicewicz et al.

(10) Patent No.: US 10,717,788 B2
(45) Date of Patent: Jul. 21, 2020

(54) CYCLODEXTRIN FUNCTIONALIZED NANOPARTICLES FOR QUENCHING BACTERIAL COMMUNICATIONS

(71) Applicant: University of South Carolina, Columbia, SC (US)

(72) Inventors: Brian Benicewicz, Columbia, SC (US); Alan Decho, Columbia, SC (US); Lei Wang, Columbia, SC (US); Kristen Miller, Columbia, SC (US)

(73) Assignee: University of South Carolina, Columbia, SC (US)

( * ) Notice: Subject to any disclaimer, the term of this patent is extended or adjusted under 35 U.S.C. 154(b) by 155 days.

(21) Appl. No.: 14/677,328

(22) Filed: Apr. 2, 2015

(65) Prior Publication Data

US 2015/0315298 A1    Nov. 5, 2015

Related U.S. Application Data

(60) Provisional application No. 61/974,046, filed on Apr. 2, 2014.

(51) Int. Cl.
| | | |
|---|---|---|
| C08B 37/16 | (2006.01) | |
| C08L 5/16 | (2006.01) | |
| A61K 47/58 | (2017.01) | |

(52) U.S. Cl.
CPC .......... *C08B 37/0012* (2013.01); *A61K 47/58* (2017.08); *C08L 5/16* (2013.01)

(58) Field of Classification Search
CPC ........ C08B 37/0012; A61K 47/58; C08L 5/16

USPC ............................................ 514/58; 536/112
See application file for complete search history.

(56) References Cited

U.S. PATENT DOCUMENTS

| | | | | |
|---|---|---|---|---|
| 5,792,821 A | * | 8/1998 | Bowen | A61K 6/0023 506/19 |
| 2013/0041112 A1 | * | 2/2013 | Benicewicz | C08F 292/00 525/342 |

FOREIGN PATENT DOCUMENTS

| | | | |
|---|---|---|---|
| WO | WO 2012/159197 | * | 11/2012 |
| WO | WO 2013/078309 | | 5/2013 |

OTHER PUBLICATIONS

Duchene et al. Cyclodextrins in targeting Application to nanoparticles. Advanced Drug Delivery Reviews 36 (1999) 29-40.*
Ke, Fu-Sheng, et al. "Tailoring nanostructures in micrometer size germanium particles to improve their performance as an anode for lithium ion batteries." *Chemical Communications* 50.28 (2014) pp. 3713-3715.

* cited by examiner

*Primary Examiner* — Yih-Horng Shiao
(74) *Attorney, Agent, or Firm* — Dority & Manning, P.A.

(57) ABSTRACT

A method is generally provided for attaching a polymer chain onto a surface of a nanoparticle, where the polymer chain comprises a cyclic arrangement of saccharides. The resulting grafted nanoparticle is also generally provided, along with its methods of use by exposing to a bacteria colony.

16 Claims, 4 Drawing Sheets

CYCLODEXTRIN FUNCTIONALIZED NANOPARTICLES FOR QUENCHING BACTERIAL COMMUNICATIONS

PRIORITY INFORMATION

The present application claims priority to U.S. Provisional Patent Application Ser. No. 61/974,046 titled "Cyclodextrin Functionalized Nanoparticles for Quenching Bacterial Communications" of Benicewicz, et al. filed on Apr. 2, 2014, the disclosure of which is incorporated by reference herein.

GOVERNMENT SUPPORT CLAUSE

This invention was made with government support under BME-1032579 awarded by the National Science Foundation. The government has certain rights in the invention.

BACKGROUND

Interference in bacterial communication is a non-cytotoxic method of controlling bacterial growth while avoiding the risk of antibiotic resistance. Bacteria communicate via autoinducer molecules to initiate activities such as pathogenesis, toxin production, and biofilm formation. A common class of autoinducers produced by bacteria is the homoserine lactone molecules. The removal of homoserine lactone molecules from the immediate bacterial environment may block their ability to communicate and subsequently establish an infection. Cyclodextrin is a truncated cone-shaped compound composed of glucopyranose units that can form an inclusion complex with homoserine lactone molecules, effectively blocking their signaling ability and hence limiting bacteria to grow and act as an infection.

SUMMARY

Objects and advantages of the invention will be set forth in part in the following description, or may be obvious from the description, or may be learned through practice of the invention.

A method is generally provided for attaching a polymer chain onto a surface of a nanoparticle, where the polymer chain comprises a cyclic arrangement of saccharides. The resulting grafted nanoparticle is also generally provided, along with its methods of use by exposing to a bacteria colony.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

DEFINITIONS

Figure 1:
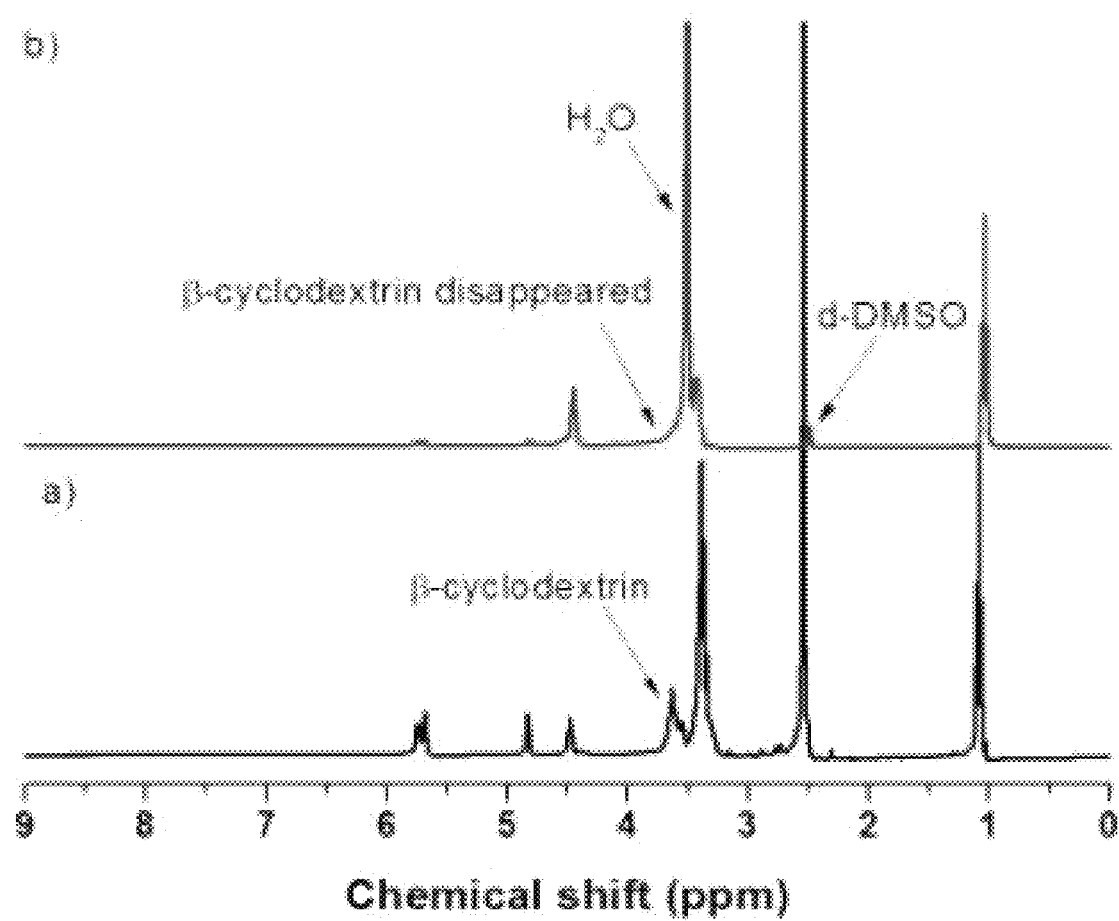
FIG. 1 shows $^1$H NMR spectra of the as-synthesized β-CD coated silica nanoparticles: a) before dialysis and b) after dialysis.

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the prefix "nano" refers to the nanometer scale (e.g., from about 1 nm to about 999 nm). For example, particles having an average diameter on the nanometer scale (e.g., from about 1 nm to about 999 nm) are referred to as "nanoparticles". Particles having an average diameter of greater than 1,000 nm (i.e., 1 μm) are generally referred to as "microparticles", since the micrometer scale generally involves those materials having an average size of greater than 1 μm.

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

The "number average molecular weight" ($M_n$) is readily calculated by one of ordinary skill in the art, and generally refers to the ordinary arithmetic mean or average of the molecular weights of the individual macromolecules. It is determined by measuring the molecular weight of n polymer molecules, summing the weights, and dividing by n, such as represented in the formula:

$$\overline{M}_n = \frac{\Sigma_i N_i M_i}{\Sigma_i N_i}$$

where $N_i$ is the number of molecules of molecular weight $M_i$. The number average molecular weight of a polymer can be determined by gel permeation chromatography, and all colligative methods, like vapor pressure osmometry or end-group determination.

The "weight average molecular weight" ($M_w$) is readily calculated by one of ordinary skill in the art, and generally refers to:

$$\overline{M}_w = \frac{\Sigma_i N_i M_i^2}{\Sigma_i N_i M_i}$$

where $N_i$ is the number of molecules of molecular weight $M_i$. The weight average molecular weight can be determined by light scattering, small angle neutron scattering (SANS), X-ray scattering, gel permeation chromatography, and sedimentation velocity.

The polydispersity index (PDI) is a measure of the distribution of molecular mass in a given polymer sample. The PDI calculated is the weight average molecular weight divided by the number average molecular weight. It indicates the distribution of individual molecular masses in a batch of polymers. The PDI has a value equal to or greater than 1, but as the polymer chains approach uniform chain length, the PDI approaches unity (i.e., 1).

As used herein the grafting density ($\sigma$) is stated in terms of chain density (chain/nm$^2$) calculated from the corresponding weight loss ratio determined by thermal gravimetric analysis (TGA), the number of grafting chains, and surface area of nanoparticles using:

$$\sigma = (wN_A/M_n)/(4\pi\alpha^2 n) = a\rho z N_A \times 10^{-21}/3(1-z)M_n$$

where w is the weight of organic polymers, $N_A$ is Avogadro's number, n is the number of nanoparticles, and z is the weight loss of polymer chains. Grafting density can also be determined by UV-V is spectroscopy methods.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Methods are generally presented to disrupt bacterial chemical communication, called quorum sensing, using nanoparticles that are engineered to bind and remove the molecules involved in chemical signaling. As stated above, cyclodextrins have shown the ability to block the signaling ability of bacteria, through reaction with the homoserine lactone molecules, to effectively limit the concentration of homoserine lactone molecules that are needed for communication. However, cyclodextrins have not been utilized to a great extent in combination with nanoparticles for investigations of quenching bacterial communications, especially in biofilm-mediated microbial infections. When carried via a nanoparticle, the concentration of cyclodextrin can be dramatically increased and the bacterial environment can be saturated with quenching compounds to block bacterial communications.

In particular, methods are generally provided to attach cyclic arrangements of saccharides (e.g., cyclodextrin) onto the surface of nanoparticles.

I. Nanoparticles

The presently disclosed methods can be utilized on a variety of different types of nanoparticles. The nanoparticle may comprise, for example, natural or synthetic nanoclays (including those made from amorphous or structured clays), inorganic metal oxides (e.g., silica, alumina, and the like), nanolatexes, organic nanoparticles, etc. Particularly suitable nanoparticles include inorganic nanoparticles, such as silica, alumina, titania (TiO$_2$), indium tin oxide (ITO), CdSe, etc., or mixtures thereof. Additionally, suitable nanoparticles can include metallic nanoparticles (e.g., Ti, gold, silver, etc.), polymer nanoparticles, carbon, graphite, graphene, carbon nanotubes, virus nanoparticles, polymer gel nanoparticles (e.g., alginate, or the like), etc., or mixtures thereof.

Nanoparticles, as used herein, includes particles (including but not limited to rod-shaped particles, disc-shaped particles, platelet-shaped particles, tetrahedral-shaped particles), fibers, nanotubes, or any other materials having at least one dimension on the nano scale. In one embodiment, the nanoparticles have an average particle size of about 1 nanometer to about 1000 nanometers, preferably 2 nanometers to about 750 nanometers. That is, the nanoparticles have a dimension (e.g., an average diameter or length) of about 1 to 1000 nm. Nanotubes can include structures up to 1 centimeter long, alternatively with a particle size from about 2 to about 50 nanometers. Due to their size, nanoparticles have very high surface-to-volume ratios.

The nanoparticles may be crystalline or amorphous. A single type of nanoparticle may be used, or mixtures of different types of nanoparticles may be used. If a mixture of nanoparticles is used they may be homogeneously or non-homogeneously distributed in the composite material or a system or composition containing the composite material. Non-limiting examples of suitable particle size distributions of nanoparticles are those within the range of about 2 nm to less than about 750 nm, alternatively from about 2 nm to less than about 200 nm, and alternatively from about 2 nm to less than about 150 nm.

It should also be understood that certain particle size distributions may be useful to provide certain benefits, and other ranges of particle size distributions may be useful to provide other benefits (for instance, color enhancement requires a different particle size range than the other properties). The average particle size of a batch of nanoparticles may differ from the particle size distribution of those nanoparticles. For example, a layered synthetic silicate can have an average particle size of about 25 nanometers while its particle size distribution can generally vary between about 10 nm to about 40 nm.

In one embodiment, the nanoparticles can be exfoliated from a starting material to form the nanoparticles. Such starting material may have an average size of up to about 50 microns (50,000 nanometers). In another embodiment, the nanoparticles can be grown to the desired average particle size.

II. Cyclic Saccharides

The cyclic saccharides are cone-shaped molecules that are able to capture bacterial communication molecules. In one embodiment, the cyclic saccharide is a cyclodextrin, cyclodextrin derivative, or a combination of cyclodextrins. Cyclodextrins are a family of compounds made up of sugar molecules bound together in a ring. Typical cyclodextrins contain a number of glucose monomers ranging from six to eight units in a ring, creating a cone shape. For example, α (alpha)-cyclodextrin is a 6-membered sugar ring molecule; β (beta)-cyclodextrin is a 7-membered sugar ring molecule; and γ (gamma)-cyclodextrin is an 8-membered sugar ring molecule.

Specific examples include the above-mentioned, but also cyclodextrins that have been derivitized, such as hydroxylated β-cyclodextrins (HP β-CD), alkylated β-CD which can afford specific properties such as increase hydrophilicity (i.e. dissolves in water).

The cyclic saccharides are arranged on long chains that are attached to the surface of the nanoparticle. Each chain contains hundreds of cyclic saccharides which allow each nanoparticle to capture a large amount of bacterial communication molecules. The molecular weight of the surface attached polymers varies, in certain embodiments, from about 500 to about 200,000 g/mol. These polymer brushes can be prepared via RAFT polymerization technique, which is able to control the molecular weight of the polymer chains.

III. Attachment of Cyclic Saccharides to Nanoparticles

As stated above, the cyclic saccharides (e.g., cyclodextrin) are attached onto the surface of nanoparticles to form grafted-nanoparticles.

a. Anchoring Compound

In certain embodiments, an anchoring compound can be attached to the surface of the nanoparticle for subsequent attachment of the polymeric chain (e.g., via a "grafting-from" or "grafting-to" approach, as described in greater detail below). The anchoring compound is covalently bonded to the surface of the nanoparticle, either directly or via a functionalization group.

The particular anchoring compound can be selected based upon the type of nanoparticle. Generally, the anchoring compound has a functional group for further reaction to the polymer chain.

For example, an anchoring compound having an amino-functionalization can be attached to the surface of a nanoparticle. In one embodiment, the amino-functionalization of the nanoparticles (i.e., attachment of amine groups to the nanoparticles) can be achieved through reaction of the nanoparticles with a mono-functional silane anchoring compound (e.g., 3-aminopropyldimethylmethoxysilane or 3-aminopropyldimethylethoxysilane). Use of a mono-functional silane as the anchoring compound, such as 3-aminopropyldimethylmethoxysilane or 3-aminopropyldimethylethoxysilane, compared to a difunctional or trifunctional silanes ensures the formation of a monolayer of anchoring agent on the silica surface and helps to prevent particle agglomeration by crosslinking during processing. However, mono-functional, di-functional, and tri-functional silanes are all suitable for use as an anchoring compound in the presently disclosed methods.

No matter the particular silane (i.e., mono-functional, di-functional, or tri-functional, etc.), the ratio of the silane to the nanoparticles is critical in determining the grafting density. In addition to adjusting the ratio by varying the concentration of the mono-functional silane, addition of a small amount of an inert dimethylmethoxy-n-octylsilane (or other alkoxy-alkyl silanes) can help to partially cover the nanoparticle surface by inert alkyl groups and to help tune the grafting density along with helping to prevent aggregation of the nanoparticles.

In addition to silanes, phosphates or their esters, phosphonates or their esters, and carboxylic acids can be used to bind to the nanoparticles surface.

b. Attaching a Cyclic Saccharide to the Anchoring Compound

The cyclic saccharide can be attached to the anchoring compound via any method. For example, the cyclic saccharide can be attached to nanoparticles via —COOH/—OH or —COOH/—NH$_2$ based coupling reactions, as well as Cu-catalyzed azide-alkyne cycloaddition (Click) reaction.

c. Bi-Modal Nanoparticles

In addition to the cyclic saccharides, other groups can be grafted to the surface of the nanoparticles to form a bi-modal nanoparticle. For example, polymeric chains can be grafted to the surface of the nanoparticles, as set forth in U.S. Patent Publication No. 2013/0041112 of Benicewicz, et al. titled "Nanoparticles with Multiple Attached Polymer Assemblies and Use Thereof in Polymer Composites," which is incorporated by reference herein.

Methods to attach such polymeric chains can vary depending on the particular functionality of the chain. See e.g., International Patent Publication No. WO 2013078309 A1 (serial no. PCT/US2012/066254) of Benicewicz, et al. titled "Silicone based nanocomposites including inorganic nanoparticles and their methods of manufacture and use;" U.S. Provisional Patent Application Ser. No. 61/927,520 of Benicewicz, et al. titled "Butadiene-Derived Polymers Grafted Nanoparticles and Their Methods of Manufacture and Use" filed on Jan. 15, 2014; U.S. Provisional Patent Application Ser. No. 61/946,956 of Benicewicz, et al. titled "Poly Alkyl (Meth)Acrylates Grafted Nanoparticles and Their Methods of Manufacture and Use" filed on Mar. 3, 2013; which are all incorporated by reference herein.

IV. Disruption of Quorum Sensing

The premise and mechanism for capturing signaling molecules using cyclodextrins is based on the diffusion of the signal molecules, and subsequent binding and capture by the hydrophobic pocket of the cyclodextrin.

Figure 2:
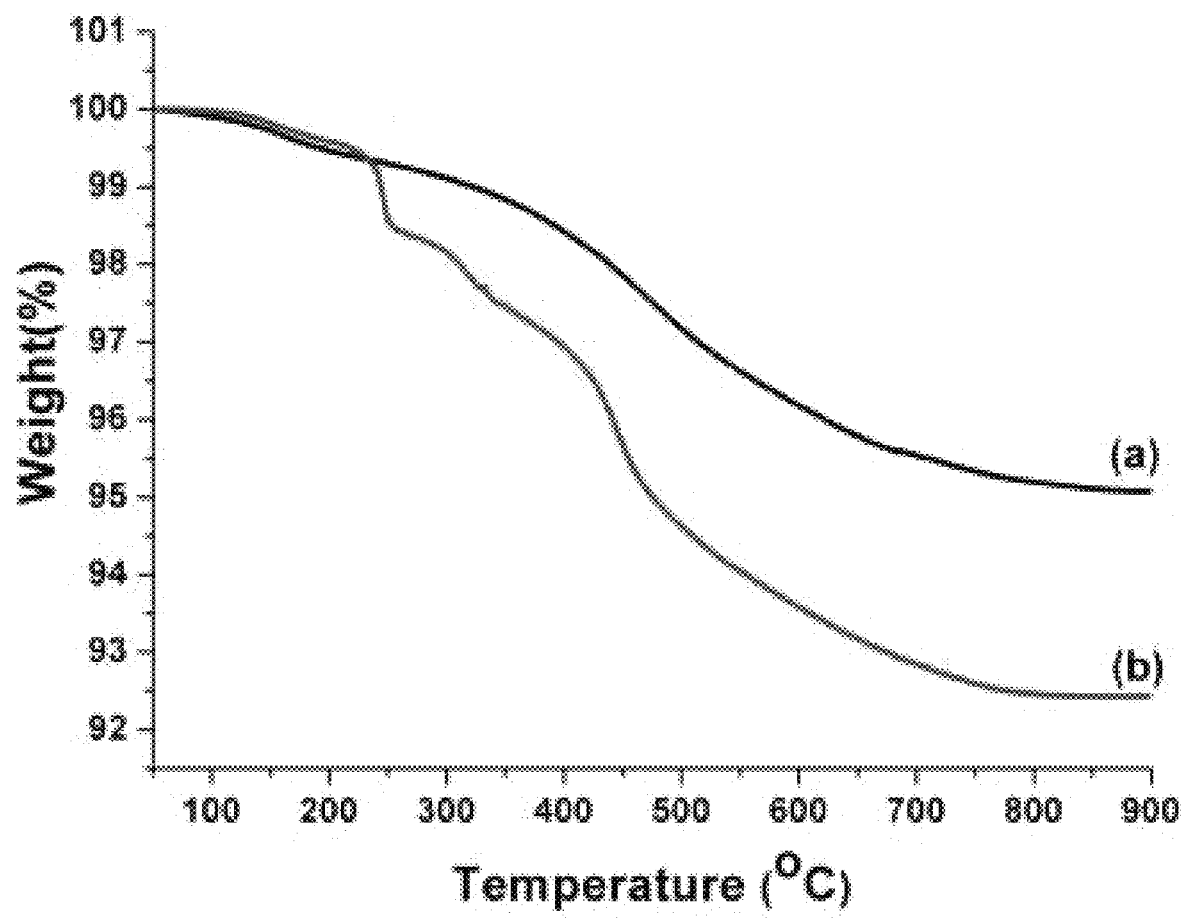
FIG. 2 shows TGA of (a) dye-labeled monolayer carboxylic acid coated silica nanoparticles (graft density: 0.24 groups/nm$^2$) and (b) dye-labeled monolayer β-CD coated silica nanoparticles.

EXAMPLES

β-Cyclodextrin (β-CD) coated fluorescent silica nanoparticles were synthesized via a coupling reaction between β-CD or functionalized β-CD and a monolayer dye-labeled carboxylic acid coated silica nanoparticles. The carboxylic acid coated nanoparticles were prepared based on a ring opening reaction between succinic anhydride and amino-functionalized silica nanoparticles with a variety of surface graft densities ranging 0.01-0.68 groups/nm$^2$. Thus, the graft density of β-CD functionalized nanoparticles can be tailored by varying the feed ratio between bare silica nanoparticles and amino-silane compound. The as-synthesized β-CD functionalized nanoparticles were purified via dialysis to completely remove un-reacted free β-CD molecules. The $^1$H NMR spectra demonstrated the β-CD coated nanoparticles without free β-CD after dialysis (FIG. 1). The TGA confirmed that the monolayer β-CD accounted for 2.78% by weight (FIG. 2).

Figure 3:
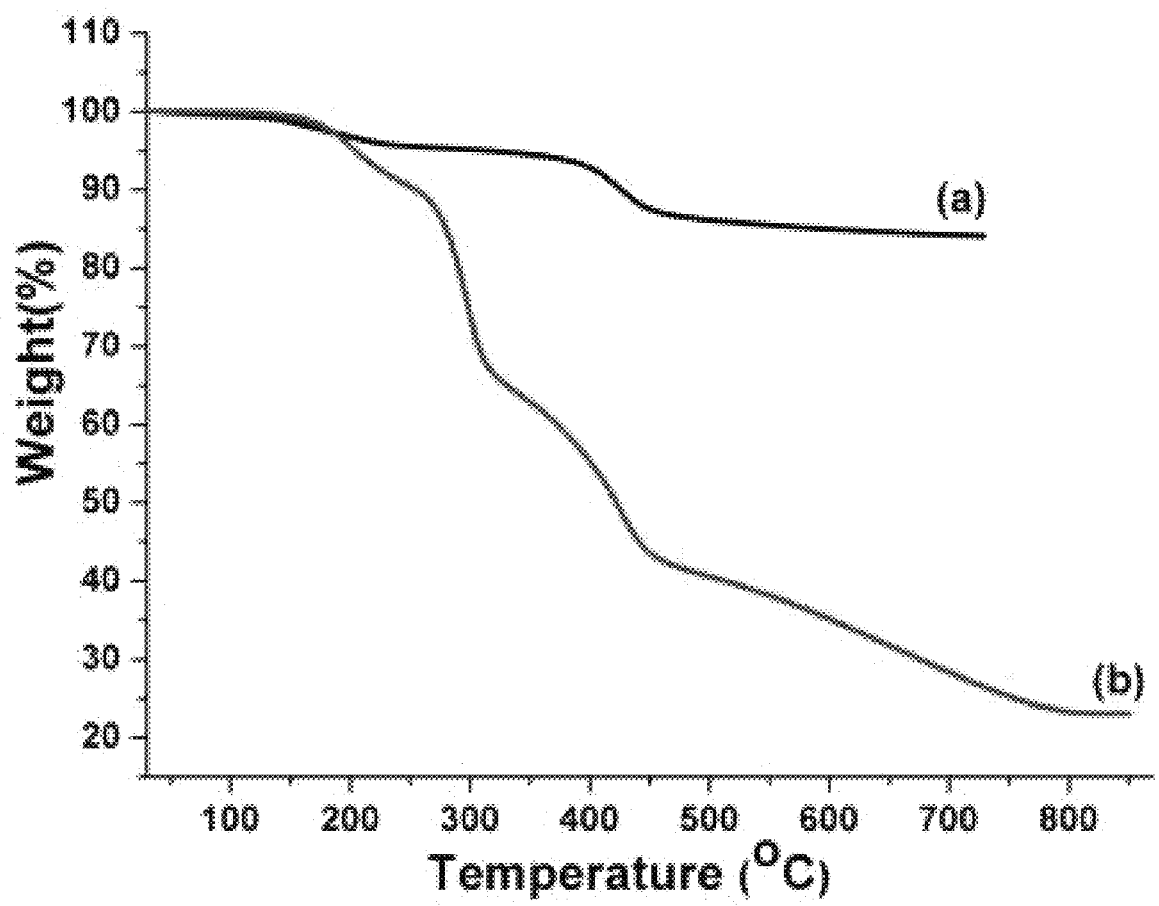
FIG. 3 shows TGA of (a) dye-labeled poly(methacrylic acid) grafted silica nanoparticles (graft density: 0.3 groups/nm$^2$) and (b) dye-labeled poly(β-CD) grafted silica nanoparticles.
Figure 4:
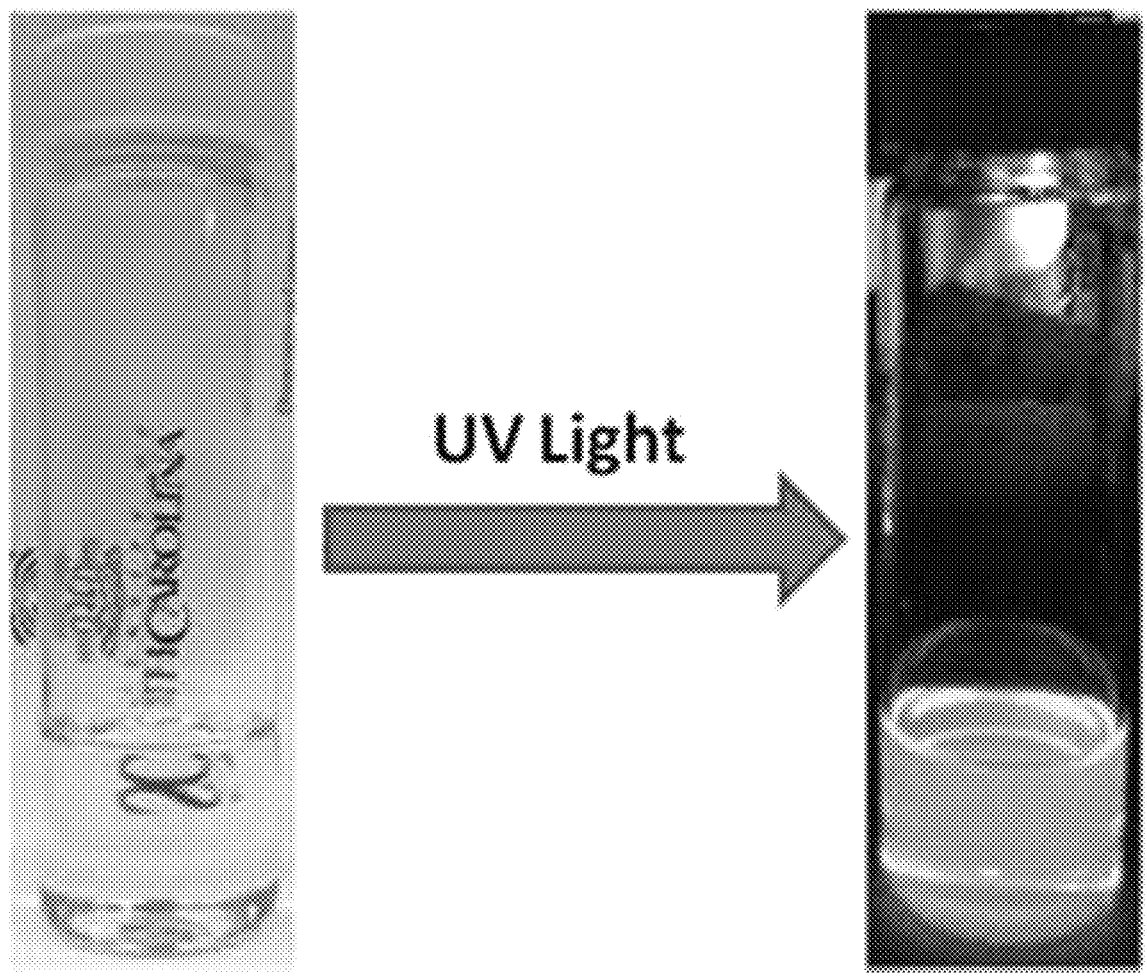
FIG. 4 shows a photograph of dye-labeled poly(β-CD) grafted silica nanoparticles in DMSO.

Silica nanoparticles with grafted polymers containing β-CD side chains were prepared via the condensation reaction between surface attached carboxylic acids or their derivatives and β-CD or functionalized β-CD. The dye-labeled poly(methacrylic acid) grafted silica nanoparticles were prepared by direct surface-initiated RAFT polymerization of methacrylic acid on dye-labeled silica nanoparticles. Thus, the β-CD loading can be controlled by tailoring the surface grafted poly(methacrylic acid) brushes length as well as the graft densities. The TGA demonstrated that the surface polymer supported multiple β-CD accounted for 61.7% by weight (FIG. 3). The β-CD side chain based polymer grafted nanoparticles showed strong fluorescence under UV light even after multiple-step surface chemical modifications (FIG. 4).

Bacteria Testing:

Phenotypic and genotypic analyses of the bioluminescent marine organism *Vibrio fischeri* indicates that cyclodextrin and cyclodextrin functionalized nanoparticles play a role in manipulating bacterial communication. The model organism *Vibrio fischeri* relies on N-octanoyl-homoserine lactone to initiate communication and regulate bioluminescence.

Growth studies show that cyclodextrin and cyclodextrin functionalized nanoparticles reduce luminescence in vitro. Quantification of gene expression during luminescence showed a decrease in the production of autoinducers and luciferase. Given that bacterial communication relies on a positive feedback loop, a decrease in production of autoinducers indicates that the level of autoinducers in the surrounding environment has also been decreased. To confirm that cyclodextrin was the active quenching agent in the model system, NMR diffusion experiments were performed.

The NMR diffusion experiments were used to demonstrate the binding affinity of cyclodextrin for N-octanoyl-homoserine lactone. Based on the dissociation constants calculated from the diffusion data, we found that N-octanoyl-homoserine lactone is able to bind cyclodextrin and form a complex, thus interfering in bacterial communications and growth.

Experimental:

Materials: All chemicals were obtained from Fisher or Acros and used as received unless otherwise specified. Trimethylsilyldiazomethane (2.0M in hexanes) was obtained from TCI. 4-Cyanopentanoic acid dithiobenzoate (CPDB) anchored silica nanoparticles were prepared according to the literature.[1] Methacrylic acid (99.5%, Acros) were purified by passing through an activated neutral alumina column. AIBN was recrystallized from methanol before use.

Instrumentation: $^1$H NMR and $^{13}$C NMR (Bruker ARX 300/ARX 400) was conducted using $CD_3OD$ as the solvent. Molecular weights and PDI were determined using a gel permeation chromatography (GPC) equipped with a 515 HPLC pump, a 2410 refractive index detector, and three Styragel columns. The columns consisted of HR1, HR3 and HR4 in the effective molecular weight ranges of 100-5000, 500-30000, and 5000-500000, respectively. The GPC used THF as eluent at 30° C. and a flow rate of 1.0 mL/min and was calibrated with poly(methyl methacrylate) standards obtained from Polymer Laboratories. The PMAA grafted nanoparticles were methylated by trimethylsilyldiazomethane[17] and then cleaved by HF before GPC analysis. Samples were filtered through microfilters with a pore size of 0.2 μm before injection. Infrared spectra were determined with a BioRad Excalibur FTS3000 spectrometer. UV-vis spectra were measured with a Perkin-Elmer Lambda 4C UV-vis spectrophotometer. Thermogravimetric analysis (TGA) was conducted using a SDT Q600 TGA system (TA Instruments) with a temperature ramping from 25° C. to 1000° C. at a rate of 10° C./min under nitrogen, and remaining at 1000° C. for 5 min.

Preparation of Monolayer Dye-labeled β-CD Functionalized Silica Nanoparticles: A DMF solution of β-CD (70.56 mg, 62.16 μmol), N,N'-Dicyclohexylcarbodiimide (DCC, 10.3 mg, 49.73 μmol) and 4-Dimethylaminopyridine (DMAP, 0.5063 mg, 4.144 μmol) was added to a 15 mL DMF solution of dye-labeled carboxylic acid-functionalized silica nanoparticles (graft density: 0.24 groups/nm$^2$, 0.7281 g). The reaction was stirred at room temperature for overnight. Then, the reaction solution was then poured into 200 mL ethyl ether followed by centrifugation at 3000 rpm for 5 min. The recovered particles were then redispersed in 20 mL of ethanol and subjected to dialysis process to further remove impurities. The dye-labeled β-CD coated silica nanoparticles were finally dissolved in ethanol/water mixture solvents for further use.

Preparation of Dye-labeled Poly(β-CD) Grafted Silica Nanoparticles: A DMF solution of β-CD (3.711 g, 3.27 mmol), N,N'-Dicyclohexylcarbodiimide (DCC, 0.54 g, 2.616 mmol) and 4-Dimethylaminopyridine (DMAP, 26.6 mg, 0.218 mmol) was added to a 10 mL dry DMF solution of dye-labeled poly(methacrylic acid) grafted silica nanoparticles (graft density: 0.30 chains/nm$^2$, 252 mg). The reaction was stirred at room temperature for overnight. Then, the reaction solution was then poured into 200 mL ethyl ether followed by centrifugation at 3000 rpm for 5 min. The recovered particles were then redispersed in 20 mL of ethanol and subjected to dialysis process to further remove impurities. The dye-labeled poly(β-CD) grafted silica nanoparticles were finally dissolved in water for further use.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method, comprising:
    attaching a plurality of polymer chains onto a surface of a nanoparticle to form a polymer brush on the nanoparticle surface, each polymer comprising a plurality of methacrylate groups; and
    attaching a plurality of cyclic saccharides to each of the polymer chains, each cyclic saccharide being attached via reaction of a methacrylate group with the cyclic saccharide.

2. The method as in claim 1, wherein the cyclic saccharides comprise cyclodextrin.

3. The method as in claim 1, wherein the cyclic saccharides comprise a cyclodextrin derivative.

4. The method as in claim 1, wherein the cyclic saccharides comprise α-cyclodextrin.

5. The method as in claim 1, wherein the cyclic saccharides comprise β-cyclodextrin.

6. The method as in claim 1, wherein the cyclic saccharides comprise γ-cyclodextrin.

7. The method as in claim 1, wherein the molecular weight of each of the surface attached polymer chains is from about 500 to about 200,000 g/mol.

8. The method as in claim 1, wherein each of the polymer chains is attached to the surface of the nanoparticle via an anchoring compound.

9. The method as in claim 1, wherein a second type of polymeric chain is also attached to the surface of the nanoparticle to form a bi-modal nanoparticle.

10. The method as in claim 1, wherein the plurality of polymer chains are attached onto the surface of the nanoparticle according to a grafting to approach.

11. The method as in claim 1, wherein the plurality of polymer chains are attached onto the surface of the nanoparticle according to a grafting from approach.

12. The method as in claim 1, wherein the plurality of cyclic saccharides are attached to each of the polymer chains following attachment of the plurality of polymer chains to the surface of the nanoparticle.

13. The method as in claim 1, wherein the plurality of polymer chains are attached onto the surface of the nanoparticle according to a direct surface-initiated Reversible Addition-Fragmentation Chain Transfer (RAFT) polymerization approach.

14. The method as in claim 1, wherein the nanoparticle is an inorganic nanoparticle, a metallic nanoparticle, or a nanoclay particle.

15. The method as in claim 1, wherein the nanoparticle comprises graphite, graphene, or carbon nanotubes.

16. The method as in claim 1, wherein the nanoparticle comprises a virus or a gel.

* * * * *